(12) United States Patent
Welch

(10) Patent No.: US 9,943,423 B2
(45) Date of Patent: Apr. 17, 2018

(54) STENT AND METHOD FOR MANUFACTURING THEREOF

(71) Applicant: Tre' Raymond Welch, Dallas, TX (US)

(72) Inventor: Tre' Raymond Welch, Dallas, TX (US)

(*) Notice: Subject to any disclaimer, the term of this patent is extended or adjusted under 35 U.S.C. 154(b) by 0 days.

(21) Appl. No.: 15/285,267

(22) Filed: Oct. 4, 2016

(65) Prior Publication Data

US 2017/0020699 A1 Jan. 26, 2017

Related U.S. Application Data

(60) Division of application No. 14/860,878, filed on Sep. 22, 2015, now Pat. No. 9,480,586, which is a continuation of application No. 12/947,767, filed on Nov. 16, 2010, now Pat. No. 9,155,640.

(60) Provisional application No. 61/261,486, filed on Nov. 16, 2009.

(51) Int. Cl.
| | | |
|---|---|---|
| *A61F 2/88* | (2006.01) | |
| *A61F 2/844* | (2013.01) | |
| *A61F 2/954* | (2013.01) | |
| *A61F 2/966* | (2013.01) | |
| *A61F 2/856* | (2013.01) | |
| *A61F 2/82* | (2013.01) | |

(52) U.S. Cl.
CPC .............. *A61F 2/885* (2013.01); *A61F 2/844* (2013.01); *A61F 2/88* (2013.01); *A61F 2/954* (2013.01); *A61F 2/966* (2013.01); *A61F 2/856* (2013.01); *A61F 2002/825* (2013.01); *A61F 2230/0069* (2013.01); *A61F 2250/0032* (2013.01); *A61F 2250/0067* (2013.01); *Y10T 29/49826* (2015.01)

(58) Field of Classification Search
CPC ...................................................... A61F 2/885
See application file for complete search history.

(56) References Cited

U.S. PATENT DOCUMENTS

| | | |
|---|---|---|
| 4,800,882 A | 1/1989 | Gianturco |
| 5,603,722 A | 2/1997 | Phan et al. |
| 5,607,445 A | 3/1997 | Summers |
| 5,632,771 A | 5/1997 | Boatman et al. |
| 5,762,625 A | 6/1998 | Igaki |
| 5,782,907 A | 7/1998 | Frantzen et al. |

(Continued)

FOREIGN PATENT DOCUMENTS

EP 2644170 A1 10/2013

OTHER PUBLICATIONS

Agrawal, C.M. et al., Evaluation of poly(L-lactic acid) as a Material for Intravascular Polymeric Stents; Biomaterials; vol. 13; No. 3; pp. 176-182; 1992.

(Continued)

*Primary Examiner* — Jacqueline Woznicki
(74) *Attorney, Agent, or Firm* — Hitchcock Evert LLP

(57) ABSTRACT

According to one aspect of the present disclosure, a method and technique for manufacturing a stent are disclosed. The stent is a non-metallic stent having a furled small-diameter state and an expanded large-diameter state where the stent, in the furled small-diameter state, includes a plurality of central lobes arranged at spaced-apart intervals and extending longitudinally defining a stent axis, the plurality of central lobes defining a cylindrical plane of the stent. The stent also includes at least one peripheral lobe formed on at least one of the plurality of central lobes, the peripheral lobe oriented along the cylindrical plane.

4 Claims, 4 Drawing Sheets

(56) References Cited

U.S. PATENT DOCUMENTS

| | | | |
|---|---|---|---|
| 6,666,881 | B1 | 12/2003 | Richter et al. |
| 6,692,521 | B2 | 2/2004 | Pinchasik |
| 7,128,755 | B2 | 10/2006 | Su et al. |
| 7,344,559 | B2 | 3/2008 | Gray et al. |
| 7,412,993 | B2 | 8/2008 | Tzeng |
| 9,155,640 | B2 | 10/2015 | Welch |
| 2003/0114916 | A1 | 6/2003 | Pinchasik |
| 2004/0098102 | A1 | 5/2004 | Richter et al. |
| 2004/0193246 | A1 | 9/2004 | Ferrera |
| 2005/0049683 | A1 | 3/2005 | Gray et al. |
| 2005/0049684 | A1 | 3/2005 | Gray et al. |
| 2005/0049685 | A1 | 3/2005 | Gray et al. |
| 2005/0049686 | A1 | 3/2005 | Gray et al. |
| 2005/0049688 | A1 | 3/2005 | Gray et al. |
| 2005/0090888 | A1 | 4/2005 | Hines et al. |
| 2005/0125053 | A1 | 6/2005 | Yachia et al. |
| 2005/0203610 | A1 | 9/2005 | Tzeng |
| 2006/0058867 | A1 | 3/2006 | Thistle et al. |
| 2007/0219619 | A1 | 9/2007 | Dieck et al. |
| 2007/0282428 | A1 | 12/2007 | Igaki |
| 2008/0071357 | A1 | 3/2008 | Girton et al. |
| 2008/0077222 | A1 | 3/2008 | Johnson et al. |
| 2008/0103584 | A1 | 5/2008 | Su et al. |
| 2008/0221670 | A1 | 9/2008 | Clerc et al. |
| 2010/0262227 | A1 | 10/2010 | Rangwala et al. |
| 2011/0106236 | A1 | 5/2011 | Su et al. |
| 2011/0118822 | A1 | 5/2011 | Welch |
| 2013/0245745 | A1 | 9/2013 | Vong et al. |
| 2016/0008150 | A1 | 1/2016 | Welch |

OTHER PUBLICATIONS

Grabow, Niels et al.; Mechanical properties of Laser Cut Poly(L-Lactide) Micro-Specimens: Implications for Stent Design, Manufacture and Sterilization; Journal of Biomedical Engineering; vol. 127; pp. 25-31; Feb. 2005.

Migliavacca, Francesco et al.; A Predictive Study of the Mechanical Behaviour of Coronary Stents by Computer Modelling; Medical Engineering & Physics; vol. 27; pp. 13-18; 2005.

Sullivan, Timothy M. et al.; Effect of Endovascular Stent Strut Geometry on Vascular Injury, Myointimal Hyperplasia, and Restenosis; Journal of Vascular Surgery; vol. 36; pp. 143-149; 2002.

Serruys, Patrick W. et al.; Coronary-Artery Stents; The New England Journal of Medicine; vol. 354; pp. 483-495; Feb. 2, 2006.

Topol, Eric J., Textbook of Interventional Cardiology; 4th Edition; Chapter 28; pp. 591-630; 2003.

Turner II, J.F. et al.; Characterization of Drawn and Undrawn Poly-L-Lactide Films by Differential Scanning Calorimetry; Journal of Thermal Analysis and Calorimetry; vol. 75; pp. 257-268; 2004.

Weir, N.A. et al., Processing, annealing and sterilisation of poly-L-lactide; Biomaterials; vol. 25; pp. 3939-3949; 2004.

Welch, Tre' R.; Vascular Stent Analysis; Presentation to the Faculty of the Graduate School of the University of Texas at Arlington in Partial Fulfillment of the Requirements for the Degree of Master of Science in Biomedical Engineering; Aug. 2005.

Welch, Tre et al.; Analysis of the Deformation During Expansion of a Bioresorable Fiber-Based Stent; BMES Annual Conference; Poster; Oct. 2006.

Welch, Tre et al.; Thermal Treatment Effects on a PLLA Bioresorbable Stent; ASME Summer Bioengineering Conference; Presentation; pp. 1-24; Jun. 2007.

Welch, Tre et al.; Influence of Thermal Annealing on the Mechanical Characteristics of a Resorbable PLLA Stent; BMES Annual Conference; Poster; Sep. 2007.

Welch, Tre et al.; Influence of Thermal Annealing on the Mechanical Characteristics of a Resorbable PLLA Stent; Southern Bioengineering Conference; Presentation; pp. 1-24; 2008.

Welch, Tre et al.; Characterizing the Expansive Deformation of Bioresorbable Polymer Fiber Stent; Annals of Biomedical Engineering; vol. 36; No. 5; pp. 74 2-751; May 2008.

Welch, Tre et al.; Thermal Treatment Improves Functional Characteristics of a PLLA Fiber Stent; BMES Annual Conference; Poster; Oct. 2008.

Welch, Tre R. et al.; The Influence of Thermal Treatment on the Mechanical Characteristics of a PLLA Coiled Stent; Journal of Biomedical Materials Research Part B: Applied Biomaterials; vol. 908; pp. 302-311; 2009 (published online Dec. 9, 2008 (www.interscience.wiley.com)).

Welch, Tre et al.; Range of Thermal Treatment upon the Mechanical Characteristics of PLLA Coiled Stents; ASME Summer Bioengineering Conference; Poster; Jun. 2009.

Welch, Tre et al; Thermal Treatment Effects Upon the Degradation Characteristics of a Bioresorbable PLLA Fiber Stent; ASME Summer Bioengineering Conference; Poster; Jun. 15, 2009.

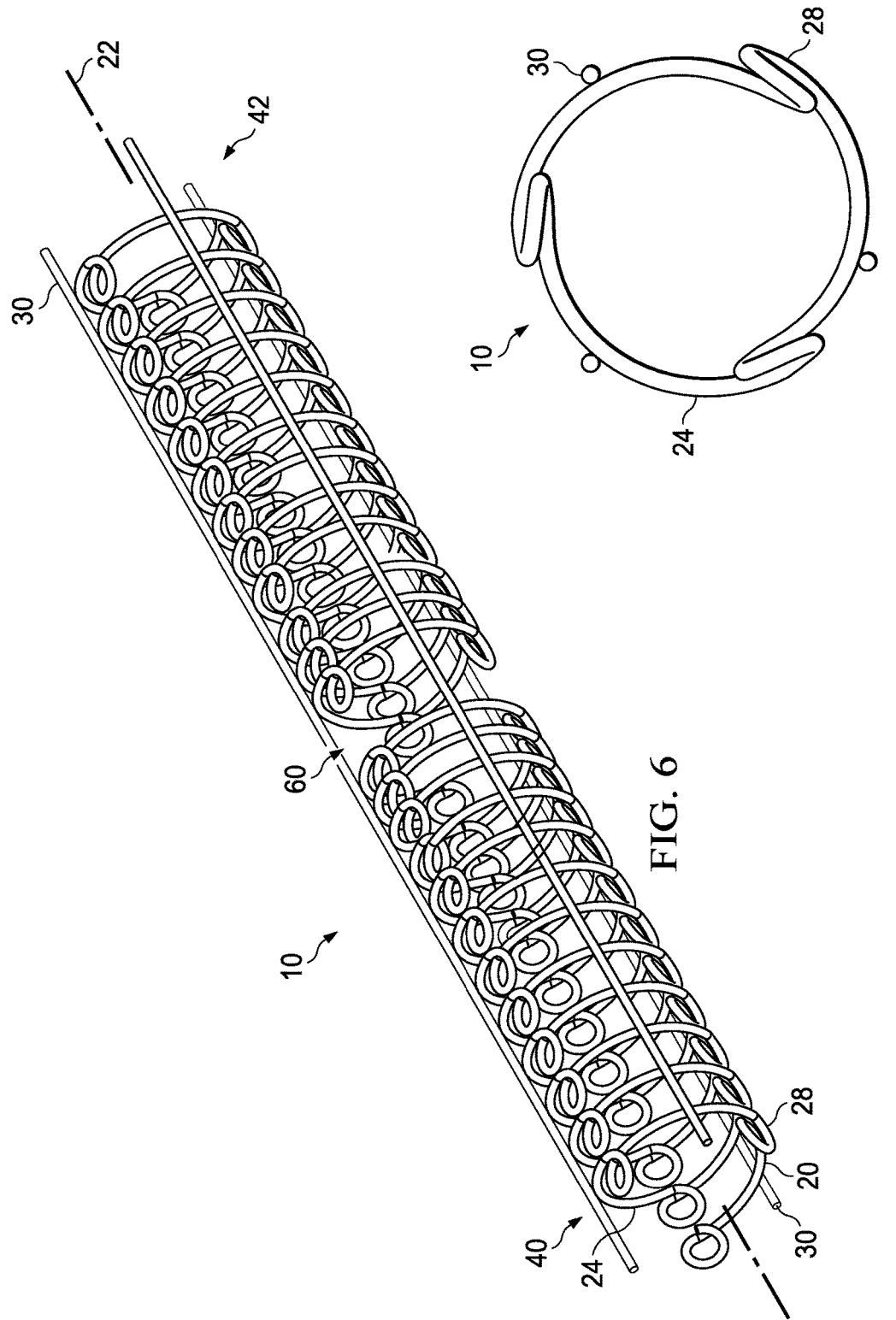

STENT AND METHOD FOR MANUFACTURING THEREOF

CROSS-REFERENCE TO RELATED APPLICATION

This application is a divisional application of U.S. application Ser. No. 14/860,878, entitled "Stent and Method for Manufacturing Thereof" and filed on Sep. 22, 2015, which is a continuation of U.S. application Ser. No. 12/947,767, now U.S. Pat. No. 9,155,640, entitled "Stent and Method for Manufacturing Thereof" and filed on Nov. 16, 2010, which claims the benefit of priority from U.S. Provisional Application No. 61/261,486 entitled "Stent and Method for Fabrication Thereof" and filed on Nov. 16, 2009. This application claims the benefit of priority from each of the above applications, which are incorporated herein by reference.

BACKGROUND

Stents are used for the treatment of various types of vascular conditions. A stent can be implanted within a vessel in a small configuration using a delivery catheter and then expanded to a larger size against the walls of the vessel.

BRIEF SUMMARY

According to one aspect of the present disclosure, a stent and method and technique for manufacturing a stent are disclosed. According to one embodiment, the stent comprises a non-metallic stent having a furled small-diameter state and an expanded large-diameter state. The stent, in the furled small-diameter state, includes a plurality of central lobes arranged at spaced-apart intervals and extending longitudinally defining a stent axis, where the plurality of central lobes define a cylindrical plane of the stent. The stent also includes at least one peripheral lobe formed on at least one of the plurality of central lobes where the peripheral lobe is oriented along the cylindrical plane of the stent.

According to another embodiment, the stent includes a first plurality of central lobes arranged at spaced-apart intervals and extending longitudinally defining a stent axis, where the first plurality of central lobes is formed by an element extending in a coiled manner from a proximal end of the stent to a distal end of the stent. The stent also includes a second plurality of central lobes arranged at spaced-apart intervals and extending longitudinally in the direction of the stent axis, where the second plurality of lobes is formed by the element returning from the distal end to the proximal end in a coiled manner. The stent further includes at least one peripheral lobe formed on at least one of the first plurality of central lobes and on at least one of the second plurality of central lobes, each peripheral lobe extending radially inward toward an internal area of the stent.

BRIEF DESCRIPTION OF THE SEVERAL VIEWS OF THE DRAWINGS

For a more complete understanding of the present application, the objects and advantages thereof, reference is now made to the following descriptions taken in conjunction with the accompanying drawings, in which:

FIG. 6 is a diagram illustrating another embodiment of a stent according to the present disclosure; and FIG. 7 is a diagram illustrating an end view of the stent illustrated in FIG. 6.

DETAILED DESCRIPTION

Figure 1:
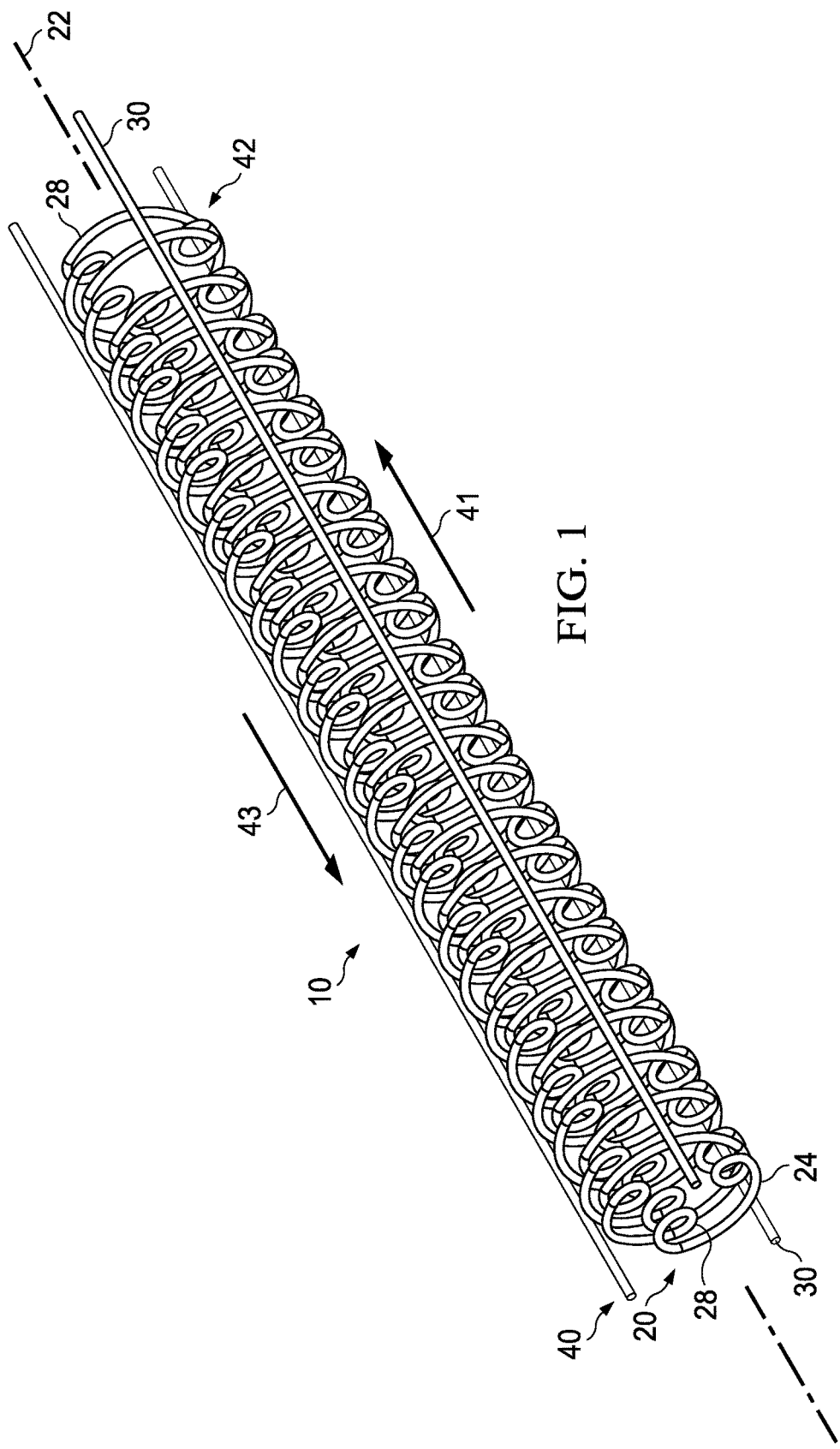
FIG. 1 is a diagram illustrating an embodiment of a stent according to the present disclosure.

FIG. 1 is a diagram illustrating an embodiment of a stent 10 in accordance with the present disclosure. FIG. 1 illustrates stent 10 in a furled small-diameter state; it should be understood that stent 10 is expandable to a large-diameter state (e.g., by balloon catheter insertion and inflation/pressurization). Embodiments of stent 10 according to the present disclosure include an element 20 disposed in a coiled manner and extending in a longitudinal direction to define a longitudinal axis 22 of stent 10. Element 20 is coiled in the direction of axis 22 to form a number of central lobes 24 (e.g., each rotation of element 20 forming one lobe 24). In some embodiments, lobes 24 are equally spaced along the longitudinal direction of stent 10 or have a uniform coil pitch along stent 10 (i.e., a uniform distance between each coil). However, it should be understood that the coil pitch may vary along one or more portions of stent 10.

In the embodiment illustrated in FIG. 1, stent 10 also includes peripheral lobes 28 formed on one or more central lobes 24. Lobes 28 are formed by additional coils of element 20 during a coil rotation of a particular lobe 24. In the embodiment illustrated in FIG. 1, each central lobe 24 includes three peripheral lobes 28. However, it should be understood that the quantity of peripheral lobes 28 formed along central lobes 24 may vary (e.g., a greater or fewer quantity). Further, in FIG. 1, each central lobe 24 includes peripheral lobes 28. However, it should be understood that some central lobes 24 may be devoid of a peripheral lobe 28, or some central lobes 24 may include a greater or fewer quantity of peripheral lobes 28 than other central lobes 24.

In some embodiments, stent 10 comprises longitudinal support rods 30 extending in the axial direction of stent 10. For example, in the embodiment illustrated in FIG. 1, stent 10 comprises three support rods 30; however, it should be understood that stent 10 may include a greater or fewer quantity of support rods 30. In some embodiments, rods 30 may be located at substantially equal distances from each other as measured about a circumference or cylindrical plane formed by lobes 24. However, it should also be understood that rods 30 may be located at unequal distances relative to each other.

In some embodiments, element 20 and/or rods 30 may comprise a nonmetallic material, such as a polymer fiber or multiple polymer fibers. For example, in some embodiments, element 20 and/or rods 30 may be formed from Poly-L-Lactic Acid (PLLA). However, it should be understood that other materials may be used to form element 20 and/or rods 30. Rods 30 may be attached or otherwise secured to lobes 24 using a variety of different methods or materials. For example, in some embodiments, rods 30 may be attached to lobes 24 using a PLLA material (e.g., PLLA dissolved in chloroform) such that the PLLA mixture is used to glue or weld rods 30 to lobes 24. In some embodiments, rods 30 may be ultrasonically welded to lobes 24. Rods 30 may be attached or otherwise secured to each successive lobe 24 along the longitudinal length of stent 10 or may be intermittently attached to lobes 24 as rod 30 extends along stent 10 (e.g., every other lobe 24, every third lobe 24, or at other uniform or non-uniform spacing intervals). Further, in some embodiments, rods 30 may be attached and/or otherwise secured to external sides of lobes 24; however, it should be understood that rods 30 may be attached and/or otherwise secured to internal sides of lobes 24. For example, in some embodiments, rods 30 may be woven or intermittently transition from an external location to an internal location of stent 10 relative to lobes 24 as rods 30 extend along the longitudinal length of stent 10. For example, and not by way of limitation, rod 30 may be secured to stent 10 by attaching rod 30 to an exterior surface of a first and second lobe 24, to an interior surface of the third lobe 24, to the exterior surface of the fourth and fifth lobes, etc. Thus, rods 30 may weave inwardly and outwardly between interior and exterior areas of stent as rods 30 extend in the longitudinal direction according to a uniform or non-uniform pattern.

In the embodiment illustrated in FIG. 1, stent 10 is formed as a dual opposing helical stent 10. For example, in the embodiment illustrated in FIG. 1, stent 10 is formed by member 20 having an end located and/or initiating at proximal end 40 of stent 10 and forming successive coils (forming lobes 24 and lobes 28) as member 20 advances in the axial direction 41 toward a distal end 42 of stent 10. At distal end 42 of stent, member 20 returns and/or is coiled in a direction 43 toward proximal end 40 forming successive coils (forming lobes 24 and lobes 28) as member 20 advances in the axial direction 43 toward proximal end 40. In FIG. 1, member 20 is wound in the same rotational direction (i.e., clockwise or counterclockwise) for forming coils in the directions 41 and 43 (e.g., clockwise winding in the direction 41, followed by clockwise winding in the direction 43). In the embodiment illustrated in FIG. 1, member 20 comprises a continuous element such that coils in both directions 41 and 43 are formed from a continuous member 20. However, it should be understood that in some embodiments, the coils formed in direction 41 may be formed from one or more members 20, where the coils formed in direction 43 may be formed by one or more different members 20.

Figure 2:
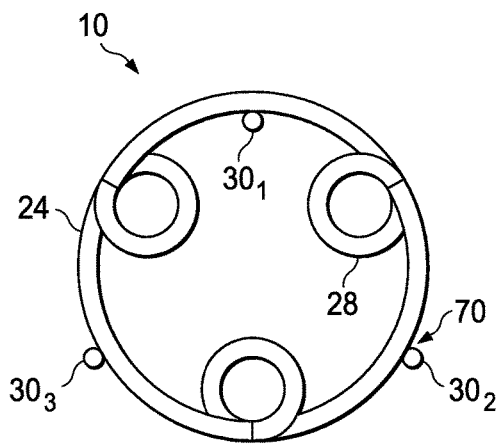
FIG. 2 is a diagram illustrating an end view of the stent illustrated in FIG. 1.

FIG. 2 is a diagram illustrating an end view of stent 10 illustrated in FIG. 1. In the embodiment illustrated in FIG. 1, stent 10 comprises three rods $30_{1-3}$ located at an equal spacing relative to each other. In the embodiment illustrated in FIG. 2, rod 301 is attached to an interior surface of lobe 24. Further, in the embodiment illustrated in FIG. 2, peripheral coils 28 extend radially inward and are located at equal circumferential spacing relative to each other. Further, in the embodiment illustrated in FIG. 2, peripheral lobes 28 formed as member 20 is coiled in opposing directions along stent 10 (e.g., extending from end 40 to end 42, then from end 42 to end 40) are located at substantially the same positions.

Figure 3:
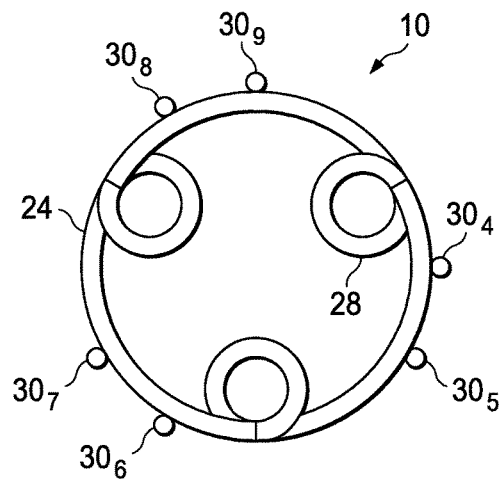
FIG. 3 is a diagram illustrating an end view of another embodiment of a stent according to the present disclosure.
Figure 4:
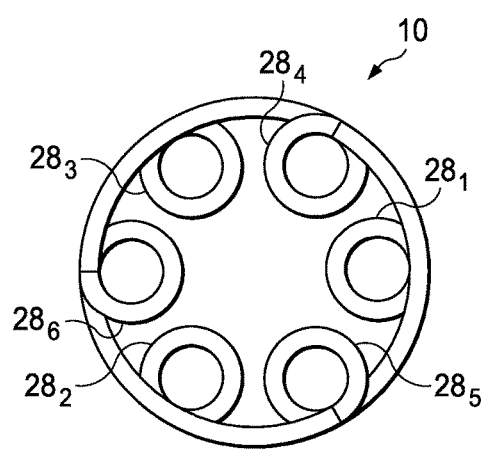
FIG. 4 is a diagram illustrating an end view of another embodiment of a stent according to the present disclosure.

FIG. 3 is a diagram illustrating an end view of another embodiment of stent 10. In the embodiment illustrated in FIG. 3, stent 10 comprises rods $30_{4-9}$ attached to exterior sides of lobes 24. In FIG. 4, some of rods $30_{4-9}$ are located at unequal distances relative to each other as measured along the cylindrical plane formed by lobes 24. For example, in FIG. 3, a set of rods $30_4$, $30_6$ and $30_8$ are located substantially equidistant from each other as measured along the cylindrical plane of stent 10, and rods $30_5$, $30_7$ and $30_9$ are located substantially equidistant from each other as measured along the cylindrical plane of stent 10. However, each set of rods 30 are offset slightly from each other such that the distance between rods $30_4$ and $30_5$, for example, is less than the distance between rods $30_4$ and $30_9$. Thus, it should be understood that the spacing of rods 30 on stent may vary.

FIG. 4 is a diagram illustrating an end view of another embodiment of stent 10. In the embodiment illustrated in FIG. 4, peripheral lobes 28 formed while member 20 is coiled in direction 41 are positioned at different locations than lobes 28 formed as member 20 is coiled in the direction 43. For example, referring to FIGS. 1 and 4, as member 20 is coiled in direction 41, peripheral lobes 28 are formed at the positions indicated in FIG. 4 by $28_1$-$28_3$. As member 20 is coiled in the direction 43 from end 42 toward end 40, peripheral lobes 28 are formed at the positions indicated in FIG. 4 by $28_4$-$28_6$. Thus, in some embodiments, lobes 28 formed as member 20 is coiled in direction 41 may be offset from the positions of lobes 28 formed as member 20 is coiled in direction 43. In FIG. 4, lobes 28 are illustrated having an equal spacing there between (e.g., corresponding to each coil direction). However, it should be understood that the spacing between lobes 28 may vary (e.g., for each individual lobe 28 and/or between coil directions 41 or 43).

In some embodiments, stent 10 is formed on a mandrel or other type of coil or winding tool to facilitate coiling of member 20 to form lobes 24 and 28 and/or to facilitate attachment of rods 30. In some embodiments, while stent 10 is located on such tool or mandrel, stent 10 is annealed to enable shape retention of the stent as well as to align and/or otherwise form polymer chain orientation characteristics. For example, in a PLLA application, stent 10 may be annealed at a temperature slightly above a glass transition temperature for a desired time period (e.g., 62° Celsius to 90° Celsius for approximately twenty-five minutes). Stent 10 may then be allowed to cool to room temperature for some period of time (e.g., eighteen hours). However, it should be understood that the annealing process may be varied, especially for different types of stent materials.

Figure 5:
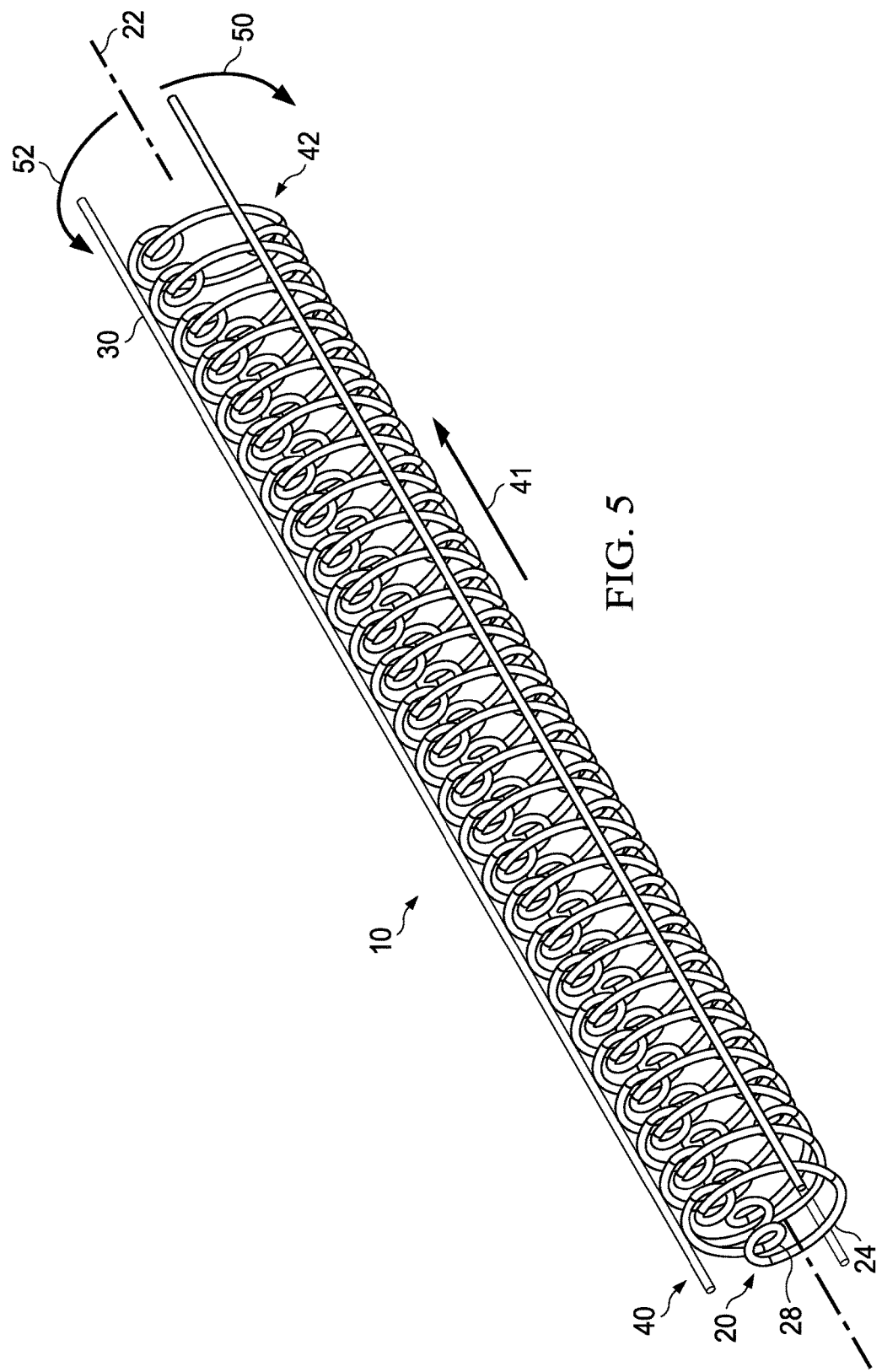
FIG. 5 is a diagram illustrating another embodiment of a stent according to the present disclosure.

FIG. 5 is a diagram illustrating another embodiment of stent 10. In the embodiment illustrated in FIG. 5, stent 10 comprises lobes 24, lobes 28 and rods 30. In FIG. 5, stent 10 is formed as a counter coil helical stent 10. For example, in the embodiment illustrated in FIG. 5, stent 10 is formed by member 20 having an end located and/or initiating at proximal end 40 of stent 10 and forming successive coils (forming lobes 24 and lobes 28) as member 20 advances in direction 41 toward distal end 42 of stent 10. At distal end 42 of stent, member 20 returns and/or is coiled in direction 43 toward proximal end 40 forming successive coils (forming lobes 24 and lobes 28) as member 20 advances in the direction 43 toward proximal end 40. In the embodiment illustrated in FIG. 5, member 20 is coiled or wound in one rotational direction for forming coils as member 20 is moved in direction 41 and is coiled or wound in an opposite rotational direction for forming coils as member 20 is moved in direction 43 toward end 40. For example, in some embodiments, the coils formed as member 20 is moved in direction 41 result from winding member 20 in the direction indicated by 50 (i.e., clockwise). The coils formed as member 20 is moved in direction 43 result from winding member 20 in the direction indicated by 52 (i.e., counterclockwise). As described above in connection with FIGS. 1-4, the spacing, quantity and locations of lobes 28 and/or rods 30 may vary. In the embodiment illustrated in FIG. 5, member 20 comprises a continuous element such that coils in both directions 41 and 43 are formed from a continuous member 20. However, it should be understood that in some embodiments, the coils formed in direction 41 may be formed from one or members 20, where the coils formed in direction 43 may be formed by one or more different members 20.

FIG. 6 is a diagram illustrating another embodiment of stent 10. In the embodiment illustrated in FIG. 6, stent 10 comprises lobes 24, lobes 28 and rods 30. In FIG. 6, lobes 28 are formed to lie substantially in the cylindrical plane formed by lobes 24. For example, FIG. 7 is a diagram illustrating an end view of stent 10 illustrated in FIG. 6. As illustrated in FIG. 7, peripheral lobes 28 are formed to lie and/or reside substantially in the cylindrical plane formed by lobes 24. In the embodiment illustrated in FIGS. 6 and 7, stent 10 includes three lobes 28 per turn or coil (e.g., per lobe 24). However, the quantity and/or spacing of lobes 28 within a particular lobe 24 may vary. Further, the quantity, spacing and/or place of attachment of rods 30 (e.g., interior surface or exterior surface of lobes 24) may vary. As described above, stent 10 may be annealed to secure and/or otherwise maintain the positioning of lobes 28 substantially within the cylindrical plane of stent 10, thereby reducing the likelihood that lobes 28 would interfere and/or obstruct the insertion of a delivery catheter into the interior area of stent 10.

In the embodiment illustrated in FIG. 6, stent 10 also comprises a bifurcated area or portion 60. For example, in some embodiments, stent 10 may be formed such that the axial pitch between successive coils in a medial portion of stent 10 is increased, thereby resulting in a location where another stent may be attached to and/or inserted through a wall of stent 10. For example, in some embodiments, the bifurcated portion 60 is formed such that the axial pitch between successive coils is large enough to accommodate a branch stent attachment to stent 10 and/or insertion of another stent through portion 60 (e.g., into a branching vessel). The medial location of portion 60 along stent 10 may vary (e.g., closer to end 40, closer to end 42, or anywhere in between). It should also be understood that bifurcated portion 60 may be included in the embodiments of stent 10 illustrated and described in connection with FIGS. 1 and 5.

In some embodiments, peripheral lobes 28 are formed having a generally circular form. However, it should be understood that the shape of lobes 28 may vary (e.g., elliptical, rhomboidal, or other non-circular shape). Further, the size of lobes 24 and/or lobes 28 may vary.

In some embodiments, a radio-opaque material may be used in stent 10 to enable x-ray and/or fluoroscopic identification of stent 10 during delivery or deployment. For example, in some embodiments, barium sulfate, water-soluble iodine and/or other materials may be laced or loaded into the polymer material used to form member 10 and/or rods 30. In some embodiments, a radio-opaque material may be used in combination with a PLLA material (e.g., PLLA dissolved in chloroform) such that the PLLA mixture having a radio-opaque material loaded therein is used to glue or weld rods 30 to lobes 24, thereby providing fluoroscopic visibility of stent 10. In some embodiments, a radio-opaque material may be attached to stent, such as securing a radio-opaque metal (e.g., platinum) to rod(s) 30 and/or member 10. The radio-opaque material may be attached using a PLLA material or other type of attachment mechanism. Further, in some embodiments, a radio-opaque sheath may be used with stent 10. For example, in some embodiments, a film comprised of a PLLA material loaded with a radio-opaque material is wrapped partially or entirely around stent 10 to enable x-ray and/or fluoroscopic identification of stent 10 during delivery or deployment.

Thus, embodiments of the present disclosure provide a flexible, expandable stent that enables increased ease and flexibility of delivery and expansion. Further, embodiments of the present disclosure provide a stent with excellent mechanical properties while providing plastic deformation.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The invention claimed is:

1. A non-metallic stent having a furled small-diameter state and an expanded large diameter state, the stent comprising, in the furled small-diameter state:
    a first plurality of central lobes arranged at spaced apart intervals and extending longitudinally defining a stent axis;
    a second plurality of central lobes arranged at spaced apart intervals and extending longitudinally along the stent axis, wherein the first plurality of central lobes and the second plurality of central lobes define a cylindrical surface of the stent; and
    at least one peripheral lobe formed on at least one of the first plurality of central lobes and on at least one of the second plurality of central lobes, wherein the at least one peripheral lobe is oriented within the cylindrical surface and extends longitudinally along the stent axis; and
    wherein each lobe of the first plurality of central lobes, the second plurality of central lobes, and the at least one peripheral lobe formed by a coiled rotation of an element; and
    wherein, as the element is rotated in a rotational winding direction, the first plurality of central lobes are formed in a first longitudinal direction along said stent axis and the second plurality of central lobes are formed in a second longitudinal direction along said stent axis to form respective first and second helices having an opposing winding pattern along the stent axis.

2. The stent of claim 1, wherein the element is loaded with a chemical agent.

3. The stent of claim 2, wherein the chemical agent is a radio-opaque agent.

4. The stent of claim 1, further comprising at least one longitudinal rod attached to one or more sides of the first plurality of central lobes and the second plurality of central lobes.

* * * * *